(12) United States Patent
Flandrois et al.

(10) Patent No.: US 9,902,988 B2
(45) Date of Patent: Feb. 27, 2018

(54) METHOD FOR ISOLATING MICROORGANISMS ON A CULTURE MEDIUM, AND RELATED DEVICE

(71) Applicant: BIOMÉRIEUX, Marcy l'Etoile (FR)

(72) Inventors: Jean-Pierre Flandrois, Lyons (FR); Bernard Limon, Rignat (FR); Christine Rozand, St Genis les Ollières (FR); Marie-Pierre Montet, Grézieu la Varenne (FR)

(73) Assignee: BIOMERIEUX, Marcy l'Etoile ( * ) Notice: Subject to any disclaimer, the term of this patent is extended or adjusted under 35 U.S.C. 154(b) by 78 days.

(21) Appl. No.: 14/415,930

(22) PCT Filed: Jul. 22, 2013

(86) PCT No.: PCT/EP2013/065451
§ 371 (c)(1),
(2) Date: Jan. 20, 2015

(87) PCT Pub. No.: WO2014/013089
PCT Pub. Date: Jan. 23, 2014

(65) Prior Publication Data
US 2015/0176048 A1    Jun. 25, 2015

(30) Foreign Application Priority Data

Jul. 20, 2012  (FR) ...................... 12 57047

(51) Int. Cl.
| C12Q 1/24 | (2006.01) |
| C12M 1/12 | (2006.01) |
| C12M 1/00 | (2006.01) |
| B32B 37/00 | (2006.01) |
| B32B 37/18 | (2006.01) |

(52) U.S. Cl.
CPC ............ *C12Q 1/24* (2013.01); *B32B 37/0038* (2013.01); *B32B 37/18* (2013.01); *C12M 25/02* (2013.01); *C12M 47/04* (2013.01)

(58) Field of Classification Search
CPC ......... C12Q 1/24; C12M 25/02; C12M 47/04; B32B 37/0038; B32B 37/18
See application file for complete search history.

(56) References Cited

U.S. PATENT DOCUMENTS

| 3,843,452 A * | 10/1974 | Freake et al. .......... C12M 23/04 |
| | | 359/397 |
| 4,565,783 A | 1/1986 | Hansen et al. |
| 2006/0211080 A1* | 9/2006 | Frost, III ............ B01F 13/0052 |
| | | 435/30 |
| 2011/0143334 A1* | 6/2011 | Roscoe .................... C12Q 1/04 |
| | | 435/5 |

FOREIGN PATENT DOCUMENTS

| EP | 0 122 581 A2 | 10/1984 |
| EP | 0 242 114 A2 | 10/1987 |
| FR | 2 182 073 A1 | 12/1973 |
| WO | 99/47637 A1 | 9/1999 |
| WO | 2005/071055 A1 | 8/2005 |
| WO | 2010/078404 A1 | 7/2010 |

OTHER PUBLICATIONS

Jan. 20, 2015 International Preliminary Report on Patentability issued in Application No. PCT/EP2013/065451.
Search Report issued in International Application No. PCT/EP2013/065451 dated Aug. 27, 2013.

* cited by examiner

*Primary Examiner* — Robert Yamasaki
*Assistant Examiner* — Teresa E Knight
(74) *Attorney, Agent, or Firm* — Oliff PLC

(57) ABSTRACT

Method for isolating microorganism from a sample likely contaminated by microorganism, including: (a) device for isolating microorganisms including a bottom waterproof layer, a nutritional layer, which is placed on the bottom layer and includes a dehydrated culture medium, an isolation layer which is pervious to elements included in the nutritional layer and is capable of retaining the bacteria on the surface and covering all or part of the nutritional layer, and a top protective layer; (b) depositing a volume of the sample on the isolation layer; (c) isolating the microorganisms by impoverishing or layering the sample using an isolating device; (d) incubating the device for an amount of time at a temperature to enable growth of microorganisms, method including at least one step of rehydrating the culture medium using a volume of liquid before or with step b) and/or c) and/or d), before or simultaneously with step b) and/or c).

6 Claims, 13 Drawing Sheets

METHOD FOR ISOLATING MICROORGANISMS ON A CULTURE MEDIUM, AND RELATED DEVICE

The present invention relates generally to the field of microbiological analysis. More particularly, it relates to a method for isolating at least one microorganism obtained from a contaminated sample.

Isolation of microorganisms on a gelled culture medium, starting from a sample to be analyzed or a suspension of microorganisms, is often an indispensable step in many methods of microbiological analysis. This step is notably used for performing identifications, verifying the microbial purity of a sample or for performing a bacterial count by counting the isolated colonies thus obtained.

The aim of the isolation techniques is to obtain, on the surface of a gelled nutrient medium, colonies that are directly usable (CDU) for identifying and determining sensitivity to antibiotics. They are well known by a person skilled in the art, the streak technique being the reference technique. The latter consists of depositing the inoculum by streaking on a surface with an equal probability per unit of area traversed. The distributed local density decreases approximately exponentially during passage of the tool. Thus, several spreading zones are prepared from a single inoculum, with or without overlapping of the zones, in order to obtain the suitable effect of distribution and a thinning out of bacteria in the next spreading segment. At the end of spreading, the cells are sufficiently isolated from one another so that microbial developments in the form of CDU (visible colonies or microcolonies) are not superposed, even partially. This technique may also be carried out by a single continuous inoculation in a spiral by means of a rotating plate or by a magnetic bead driven by a device producing continuous inoculation that is not overlapping or optionally is partially overlapping.

Another widely used technique consists of isolation on a dish of gelled medium by spreading on the surface. In this case, a mixture of cells at a low cellular concentration allowing 30 to 300 cells to be put in culture is spread on the surface of the gel in a Petri dish with a diameter of 9 cm, each cell developing into an isolated colony. When fewer than 30 cells are brought into contact with the nutrient gel, statistical problems affect the accuracy of the count.

When the number counted is above 300 cells, counting errors arise owing to overlapping of the surfaces of the colonies. Spreading is usually effected with a tool comprising for example a linear part that is in contact with the gel or using beads a few millimeters in diameter rolling randomly on the surface in disordered movement. This technique is only suitable for a slightly contaminated or diluted sample as a high number of cells increases the probability of confluence of the colonies as a result of growth.

It is also possible to perform isolation on a dish by deep inoculation. The initial sample is diluted several times so as to reduce the microbial population sufficiently and obtain separate colonies. Small volumes of each of the diluted samples are then mixed with a liquid gel, usually of agar supercooled to about 45° C. The mixtures are immediately poured into sterile culture dishes and after gelling and incubation, each cell is immobilized and forms a colony.

Certain manual methods have been automated owing to the development of devices. This is so for example in the case of document EP-0 242 114, which describes equipment and a method for inoculation of a culture medium with a sample. The method consists of performing several segments of spreading from one inoculum. These segments are in the form of circular arcs and are performed by means of four different spreading heads. An effect of dilution of the sample is obtained by partial overlapping of the subsequent segments. The method described in the document is in fact very similar to the reference method of manual isolation.

More recently, new methods of isolation have been developed, allowing improvement of bacterial exhaustion by using an optimized applicator as described in document WO-A-2005071055. This applies notably to the method of inoculation employed in the automatic device marketed by the applicant under reference PREVI™ Isola.

However, these isolation techniques are only effective on gelled culture media.

In the areas of clinical diagnostics and of industrial microbiological control in the food, pharmaceutical or cosmetics industry, gelled culture media in a Petri dish, most often agar, have constituted, since the end of the 19th century, an indispensable tool for the detection and identification of pathogenic microorganisms.

However, a great many products have been developed for replacing the Petri dish. For these products, rehydration is carried out in situ, i.e. directly in the space serving for inoculation and for incubation. One of these, the Petrifilm™ system, comprising rehydratable nutrients, is very widely used. Another system developed by the company Nissui Pharmaceutical, Compact Dry, also consists of a dehydrated medium. These culture media have the advantage that they keep longer than a ready-to-use agar culture medium. They may also, like Petrifilm™, be compact and thus use a small incubation space. The surface available for culture is limited and the nutrients available per cell are of suitable concentration to give colonies of smaller diameter than on conventional gelled medium, and the form of the colonies may also be modified owing to the low solidity of the gel used or high coefficients of diffusion of the bacteria.

Nevertheless, isolation of colonies on these media is only possible by inclusion in the gel formed during rehydration, and therefore from an initial sample with low level of contamination or that has undergone a series of dilutions. The final concentration to be deposited on the medium must be under 300 CFU/ml (CFU: colony forming unit), these conventional data depending on the size of the colony.

Moreover, these media cannot withstand the mechanical stress of a means of isolation by exhaustion without undergoing deterioration. Thus, one of the major problems of these culture media that are rehydratable in situ, i.e. directly in the space serving for inoculation and incubation, is that they are not compatible with manual or automated mechanical isolation of microorganisms. When the initial sample is heavily contaminated (above 300 CFU/ml), they require a series of dilutions to be carried out, meaning taking a larger sample, loss of time and the consumption of a large number of reagents (culture medium, tubes of diluents, etc.), generating a large volume of waste (autoclaving, cost of treatment). Moreover, if a large number of dilutions is carried out, there is a risk of losing, by the dilution effect, the target pathogenic microorganism, if the latter is present in a small amount relative to the total microflora.

It is clear from the prior art considered that no method of isolation is available that is simple to carry out starting from a sample to be analyzed or a bacterial suspension, on a culture medium rehydratable in situ, which allows isolated colonies to be obtained.

A first aim of the present invention is therefore to supply a method for isolating microorganisms and a related device that offer better performance and are simpler to apply than the methods and devices of the prior art.

A second aim of the present invention is to supply a device and a method for isolating microorganisms that can be used on a culture medium that is rehydratable, or rehydrated just before or simultaneously with microbial isolation, directly in the space serving for inoculation and incubation.

A third aim of the present invention is to supply a method for isolating microorganisms from a sample having a high initial microbial concentration.

A fourth aim of the present invention is to supply a method of isolation that is also compatible with counting of the microorganisms.

A fifth aim of the present invention is to supply a device and method of isolation compatible with the use of chromogenic media.

These aims, among others, are achieved by the present invention, which proposes a method for isolating at least one microorganism from a sample that may be contaminated with said microorganism, comprising the following steps:
  (a) supplying a device for isolation of microorganisms comprising
    a bottom layer impermeable to water
    a nutrient layer, arranged on the bottom layer, comprising a dehydrated culture medium
    an isolating layer permeable to the elements comprised in the nutrient layer, able to retain the bacteria on its surface and covering the whole or a portion of the nutrient layer
    a protective top layer
  (b) depositing a defined volume of the sample on the isolating layer
  (c) isolating the microorganisms by exhaustion or by coating the sample using isolating means,
  (d) incubating the device for a predetermined time and at a predetermined temperature allowing growth of the microorganisms
said method also comprising at least one step of rehydration of the culture medium with a predetermined volume of liquid before or simultaneously with step b) and/or c) and/or d), preferably before or simultaneously with step b) and/or c).

According to a preferred embodiment, the device mentioned in step a) is obtained by the method comprising the following steps:
  pouring said predetermined volume of liquid onto the layer impermeable to water,
  arranging the isolating layer on the nutrient layer, the whole being placed on the layer impermeable to water that previously received said predetermined volume of liquid in order to allow instantaneous and homogeneous rehydration of said dehydrated culture medium, and
  then superposing the protective top layer.

In other words, said device is advantageously obtained by successive superposition of the following layers: 1) layer impermeable to water (preferably having received said predetermined volume of liquid), 2) nutrient layer, 3) isolating layer and 4) protective top layer, at least the nutrient layer 2) and isolating layer 3) being mechanically independent of one another, so that they can easily be separated. This notably offers the advantage that each of the two layers mentioned above can be sold and/or stored separately. They can then easily be superposed by the user. Preferably, all the layers are mechanically independent of one another, so that they can easily be separated from one another.

"Layers mechanically independent of one another" means layers that are not joined together by at least one bonding means, said bonding means that may notably be of a:
  physical nature, for example one or more clamps, or
  chemical nature, such as glue, melting of some or all of the two layers under the action of a solvent to give rise to a composite/hybrid layer (also called "bonding layer"), or else a gel or a gelling agent that is interposed at least partially between said layers (namely at least partially at the interface between said layers).

Besides the aforementioned advantage (separate selling and/or storage of the nutrient and isolating layers), the applicant discovered, against all expectations, that omitting a bonding means forming an interface between the nutrient layer and the isolating layer makes it possible, by reducing the distance between these two layers, to obtain better growth and/or survival of the microorganisms deposited on the isolating layer. In fact, a bonding means of this kind is of such a nature that it slows the passage of the nutrients from the rehydrated nutrient layer to the microorganisms present on the isolating layer, thus reducing the growth and/or the chances of survival of these microorganisms.

Sample means a small portion or small amount separated from an entity by a subtractive act usually called sampling, for purposes of analysis.

The sample may be of biological, human, animal, vegetable or environmental origin. It may relate to a product in the course of an industrial process or a finished product, for example food. It may therefore correspond to a sample of biological fluid (whole blood, serum, plasma, urine, cerebrospinal fluid, organic secretion), a tissue sample or sample of isolated cells. It may be of industrial origin, i.e., according to a nonexhaustive list, a sample of air, a sample of water, sampling from a surface, a piece or a product in the course of treatment or manufacture, a product of food origin. Among samples of food origin, we may mention nonexhaustively a sample from milk products (yoghurts, cheeses, etc.), meat, fish, eggs, fruits, vegetables, water, drinks (milk, fruit juices, soda, etc.) and the constituent or ancillary products of the finished product. A food sample may finally be obtained from feed intended for animals, such as notably meal as animal feed. Before analysis, this sample may undergo preparation such as enrichment, extraction, concentration, purification, by methods known by a person skilled in the art. According to a preferred embodiment, the sample volume deposited on the culture medium is between 10 and 1000 μl.

In the sense of the present invention, the term microorganism covers Gram-positive or Gram-negative bacteria, yeasts, molds, amoebae and, more generally, unicellular organisms, invisible to the naked eye, which can be manipulated and multiplied in the laboratory.

According to a preferred embodiment of the invention, the microorganism is a Gram-negative or Gram-positive bacterium, or a yeast.

As Gram-positive bacteria, we may mention the bacteria of the following genera: *Enterococcus, Streptococcus, Lactobacillus, Bifidobacterium, Staphylococcus, Bacillus, Listeria, Clostridium, Mycobacteria, Nocardia, Corynebacteria, Micrococcus* and *Deinococcus*.

As yeasts, we may mention the yeasts of the following genera: *Candida, Cryptococcus, Saccharomyces* and *Trichosporon*.

As molds, we may mention the molds of the following genera: *Aspergillus, Penicillium, Cladosporium*.

The present invention also relates to a device for culture of microorganisms comprising a bottom layer impermeable to water a nutrient layer, arranged on the bottom layer, comprising a dehydrated culture medium an isolating layer permeable to the elements comprised in the nutrient layer, able to retain the bacteria on its surface and covering the whole or a portion of the nutrient layer a protective top layer.

Preferably, the nutrient layer and the isolating layer are mechanically independent of one another, as already mentioned.

In the sense of the present invention, the nutrient layer comprises a support containing a dehydrated culture medium. The support may be based on various absorbent compounds with very strong water retentivity such as rayon, cotton, natural or chemically-modified cellulose fibers such as carboxymethylcellulose, absorbent or super-absorbent chemical polymers such as polyacrylate salts, acrylate/acrylamide copolymer. This support may be impregnated with a culture medium in liquid form and then dehydrated, i.e. having an Aw (activity of water) incompatible with microbial development. Alternatively, it is covered or impregnated dry with a culture medium or its constituents in the form of powder. Alternatively, liquid impregnation may, after dehydration, be supplemented by adding powder according to the means described above.

Culture medium means a medium comprising all the elements necessary for the survival and/or growth of microorganisms. In practice, a person skilled in the art will select the culture medium as a function of the target microorganisms, according to criteria perfectly known and within the capability of the person skilled in the art.

The nutrient layer according to the invention may contain optional additives, for example: peptones, one or more growth factors, carbohydrates, one or more selective agents, buffers, dyes, one or more gelling agents, hydrogels, viscous agent, etc.

Preferably, the medium contains little or no cold gelling agents, such as, for example, agar, agarose, poloxamers, guar gum, xanthan, etc. Generally, the nutrient layer may in addition contain a substrate allowing detection of an enzymatic or metabolic activity of the target microorganisms based on a signal detectable directly or indirectly. For direct detection, this substrate may be bound to a part serving as fluorescent or chromogenic marker. For indirect detection, the nutrient layer according to the invention may in addition comprise a pH indicator, sensitive to the pH change induced by the consumption of the substrate and revealing growth of the target microorganisms. Said pH indicator may be a chromophore or a fluorophore. As examples of chromophores, we may mention neutral red, aniline blue, bromocresol blue. The fluorophores comprise for example 4-methylumbelliferone, hydroxycoumarin derivatives or resorufin derivatives. Thus, the PC-PLC fluorescent substrate preferably used for carrying out the method according to the invention corresponds to 4-methyl-umbelliferyl-choline phosphate (4 MU-CP).

According to a preferred embodiment of the invention, after dry impregnation of the nutrient layer with the dehydrated culture medium, the latter undergoes a calendering operation. Calendering, by the pressure and heating temperature generated, allows retention and stable maintenance over time of the dehydrated culture medium in the nutrient layer, ensuring retention of the nutrients in the nutrient layer. It also makes it possible to obtain a rigorously smooth and flat surface of the nutrient layer. This is particularly advantageous for ensuring good cohesion between the nutrient layer and the isolating layer when the latter is arranged on the nutrient layer. Besides accelerating the rehydration of the nutrient layer relative to an uncalendered nutrient layer, calendering allows compression of the fibers constituting the nutrient layer. This compression, combined with the presence of the dehydrated medium within the nutrient layer, generates a large increase in capillary capacity of the latter, causing its almost instantaneous rehydration and generating a phenomenon of aspiration of the isolating layer arranged on its surface. The isolating layer is then flattened against the nutrient layer (while being mechanically independent of the latter), thus ensuring absence of space between the two layers and in consequence optimal microbial growth and/or survival on the entire surface of the isolating layer. There is thus no need to have recourse to a bonding means (for example a bonding layer) between the isolating layer and the nutrient layer. This represents a significant advantage, in that said bonding means slows passage of the nutrients from the rehydrated nutrient layer to the microorganisms present on the isolating layer, thus reducing growth and/or the chances of survival of these microorganisms.

As noted above, the possibility of separating the nutrient layer and the isolating layer, thus allowing the two layers to be sold and/or stored separately, represents a real industrial bonus. Such a technical effect then allows the nutrient and isolating layers to be considered independently of one another, including from a commercial and/or logistic (storage) standpoint. This represents a significant advantage for the user, who is notably able to combine at will nutrient and isolating layers with different properties, suitable for the microorganisms to be detected.

Isolating layer means a layer whose main constituent is a material which by its nature, its size, and its steric arrangement, retains the microorganisms on its surface while being permeable to the elements comprised in the nutrient layer located beneath the isolating layer.

The isolating layer may be based on one or more materials or derivative of these materials such as latex, polytetrafluoroethylene, poly(vinylidene) fluoride, polycarbonate, polystyrene, polyamide, polysulfone, polyether-sulfone, cellulose, a mixture of celluloses and nitrocellulose. Advantageously, the isolating layer is porous, preferably it is a porous membrane permeable to the elements comprised in the nutrient layer, able to retain the microorganisms on its surface and covering the whole or a portion of the nutrient layer. The applicant discovered that the membranes for microfiltration of water (and generally of liquids) currently marketed generally have the properties required for use as the isolating layer. They make it possible to obtain very good resistance to tearing during manipulation, controlled porosity, a perfectly smooth character, small thickness and most of the time are highly hydrophilic. Their color, generally white, makes it possible to optimize differentiation of stained colonies on their surface. The applicant discovered, surprisingly, that the use of these filtration membranes not for a function of "traditional" filtration of liquids (as is done for water or generally for liquids) but as a support that is smooth and strong for isolating the test sample on their surface was particularly suitable for carrying out the present invention. Regarding the filtration capacity and the hydrophilicity of the filtration membrane, they are utilized in order to allow and optimize passage of the liquid nutrients present in the nutrient layer (after rehydration thereof) to the isolating layer while preventing the bacteria, yeasts and molds seeded on the surface of the isolating layer from migrating in the opposite direction.

For the purposes of the present application, the aforesaid filtration membranes are designated either as "filtration membranes", or "microfiltration membranes" or else "filtering membranes", these expressions being synonyms of one another. These filtration membranes are comprised in the group consisting of the porous membranes.

In one embodiment of the invention, the isolating layer is active. It may thus contain specific sites that are receptors of bacteria such as antibodies or fragments of antibodies, bacteriophages or fragments of bacteriophages, aptamers or any specific ligands that may be fixed covalently or indirectly by similar biochemical elements, at least one of which is fixed covalently, for example a system using streptavidin and biotin.

Alternatively, the isolating layer is active, containing compounds that inhibit or destroy bacteria such as bacteriophages, antibacterial peptides, antibiotics, which may or may not be fixed in or on the isolating layer. The compounds may be fixed covalently or indirectly by related biochemical elements. Moreover, in another embodiment of the invention, the isolating layer is active, containing elements that stimulate or accelerate growth of the microorganisms. As an example, a viscous agent such as polyethylene glycol is arranged on the isolating layer.

Isolation may be carried out on some or all of the isolating layer, defining the useful surface for isolation.

The isolating layer consists of a surface allowing passage of the elements from the nutrient medium and selective or reactive agents.

Advantageously, the isolating layer comprises pores whose diameter is between 0.01 and 0.8 µm and preferably between 0.2 µm and 0.6 µm so as to retain the bacteria, yeasts and molds on its surface. According to a particular embodiment, the isolating layer comprises pores whose diameter is between 0.25 µm and 0.6 µm, for example between 0.3 µm and 0.6 µm, or else between 0.4 µm and 0.6 µm.

Alternatively, it may be a layer that does not have measurable pores, such as a dialysis membrane, a cellulose membrane permeable to water and to chemical compounds and defined by its capacity for retention of compounds with a molecular size above a threshold. Advantageously the membrane will allow retention of chemical molecules with a molecular weight greater than 500 000 dalton (or between 5000 and 500 000 dalton).

Advantageously, the isolating layer comprises confined zones that make it possible to facilitate isolation of the microorganisms. They may also make it possible to reduce the growing time and therefore obtain the result more quickly.

In one embodiment, the isolating layer has hydrophobic and/or hydrophilic units spatially delimiting the growth of the bacteria. The size of hydrophilic unit is between 10 and 500 µm, preferably between 300 and 500 µm, namely a diameter greater than the resolving power of the eye. When it is a question of classic microbiology and therefore visual observation.

In another embodiment, the isolating layer contains nanostructured units, incompatible with microbial growth, delimiting confined zones allowing growth of the microorganism.

The hydrophobic units are arranged in the form of a surface pattern which is a regular or irregular grid, an assembly of regular or irregular hexagons or according to a mixture of the two patterns, or optionally of other forms.

The desirable materials for making this hydrophobic unit include wax, hydrophobic ink, epoxy resins, silicone oil, silicone wax, polystyrene resin, alumina, polyfluoroethylene, etc.

The isolating layer covers the whole or a portion of the nutrient layer. The isolating layer is positioned on the nutrient layer, partly covering it in order to allow rehydration of the medium by a liquid. In a preferred embodiment, the nutrient layer may be covered by the isolating layer completely.

The device may contain at least one rehydrating means in contact with the nutrient layer such as a reservoir attached to the device or included in the latter and/or channels allowing rehydration of the bottom part or lateral part of the nutrient layer, preferably of the bottom part of the latter.

The useful surface for isolation may be surrounded by a zone that does not allow microbial development. It may be a zone made of an impermeable material or a hydrophobic zone. Advantageously, said zone may be structured for guiding manual use.

"Isolating means" is to be understood as a means allowing the microorganisms to be brought into contact with the culture medium by moving over the latter in order to deposit the sample. As the sample becomes impoverished as rubbing takes place between the sample and/or the isolating means and the isolating layer, isolated cells are deposited, so that after growth, isolated colonies may be obtained.

The isolating means has one or more surface(s) of contact with said culture medium. Such a means may be used manually, for example a loop, a platinum loop, a pipette, a ground rod, a rod comprising a terminal ball, a swab. It may also be beads.

Advantageously, the method according to the invention may be implemented by means of an automated system. A particularly suitable system is the PREVI™ Isola system such as is protected in patent application WO-A-2005071055 and is marketed by the applicant.

According to the invention, the culture medium is rehydrated with a predetermined volume of liquid.

A suitable volume of liquid is propagated in the culture medium. In practice, a person skilled in the art will select the appropriate volume of liquid as a function of the viscosity of the liquid, the diameter of the nutrient layer, in order to rehydrate the medium and allow growth of the microorganisms. The rehydration step takes place before or simultaneously with step b) and/or c) and/or d), preferably before or simultaneously with step b) and/or c). In a particular embodiment, the liquid is added manually using a pipette, or automatically. In another embodiment, the liquid is contained in at least one reservoir integrated with the device and/or channels allowing rehydration of the nutrient layer. The liquid then spreads in the nutrient layer by simple pressure of the reservoir. An advantage of rehydration via the bottom and/or lateral part, preferably via the bottom part, is that it allows uniform hydration of the entire nutrient layer. This embodiment notably prevents the nutrients of the nutrient layer being entrained by the liquid into the bottom part of the device.

According to one embodiment of the invention, the liquid used for reconstituting the culture medium is an aqueous solution. According to a particular embodiment, the liquid contains microparticles with lipid envelopes, and preferably the liquid contains red blood cells.

The liquid may also be a buffer or a solution containing supplements of the culture medium, such as antibiotics or substrates.

According to the invention, the device comprises on either side of the nutrient layer and the isolating layer
- a bottom layer impermeable to water
- a protective top layer.

The top layer may be translucent or transparent so that the colonies are visible through this layer. Preferably, the protective top layer is separated from the colonies by a separating means. The separating means may be a side wall or any other means allowing the top layer not to be in contact with the colonies.

Advantageously, the top layer will be able to rest on the parts of the isolating layer that do not allow microbial development, such as the peripheral zones or the hydrophobic units.

The top layer may be attached by one of the sides to one of the other layers of the device by any means, namely for example an adhesive or mechanical means.

It also makes it possible to prevent contamination during incubation. It is impermeable to bacteria and limits the loss of water vapor. In fact, the device is incubated for a predetermined time and at a predetermined temperature allowing growth of the microorganisms independently of the ambient humidity conditions. Thus, the nature of the top layer is selected so as to allow the gaseous exchanges necessary for growth of the microorganisms while allowing local hydration. The bottom layer is impermeable to water. Preferably, this bottom layer is rigid, allowing better grip of the device in the hand. It is manufactured from compounds such as polyester, polypropylenes, polystyrene. Preferably, it is manufactured from cellulose. It may be cardboard or paper combined with a film impermeable to water. It may contain thermoformed channels that will serve for proper rehydration of the nutrient layer.

Advantageously, the various layers of the device are made from recyclable materials.

According to a particular embodiment of the invention, the bottom layer and/or the nutrient layer and/or the isolating layer is/are translucent or transparent.

According to a particular embodiment of the invention, the device also comprises an identification code such as barcodes or RFID tags.

A device according to the invention may be of conventional shape, namely of round shape. It may nevertheless be of a different shape and notably of square or rectangular shape. According to another variant, the various layers may be of different shapes. Thus, for example, the top, bottom and nutrient layers may be of square shape and the isolating layer and/or surface useful for isolation of round shape. The various layers may be of different colors, facilitating discrimination of the suspected bacteria.

The invention also relates to the use of a device according to the invention.

The invention, its functionality, its applications as well as its advantages will be better understood on reading the present description, referring to the figures, in which:

FIGS. 1A and 1B are schematic representations of the device according to the invention. The device 10 comprises a bottom layer impermeable to water 14, a nutrient layer 12, arranged on the bottom layer, comprising a dehydrated culture medium, an isolating layer 20 permeable to the elements comprised in the nutrient layer, able to retain the bacteria on its surface and covering the whole or a portion of the nutrient layer, a protective top layer 15. This device also comprises hydrophilic/hydrophobic zones 13, a reservoir 19 and channels 18 allowing rehydration of the bottom part or lateral part of the nutrient layer. The device may have separating means 16 allowing the top layer 15 not to be in contact with the colonies.

EXAMPLES

Figure 1A:
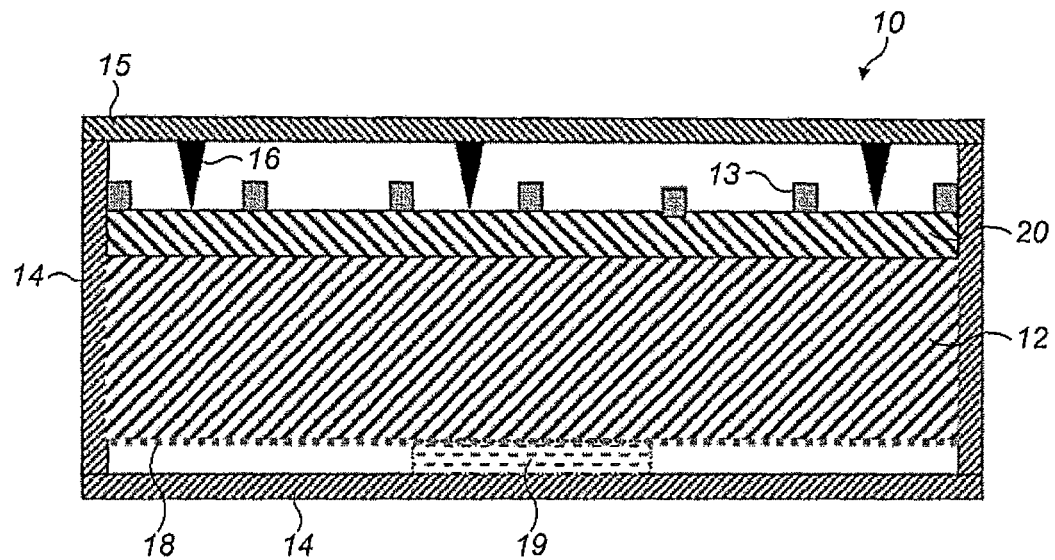
Figure 1B:
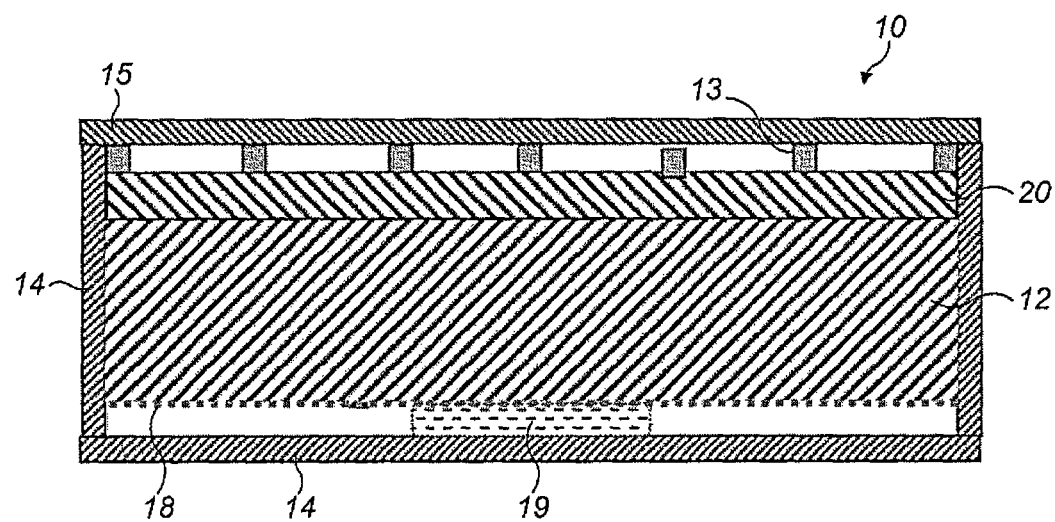

Example 1: Obtaining Isolated Colonies from a Heavily Contaminated Solution on a Petrifilm Rehydrated Medium From a solution calibrated at a theoretical bacterial load of $10^8$ CFU/ml, 1000 µl of solutions loaded with *Escherichia coli* at different concentrations obtained by successive dilutions by a factor of 10 are deposited at the center of the bottom film of Petrifilm®. The top film of Petrifilm® is lowered onto the sample. A plastic diffuser, concave face downwards, is placed at the center of the Petrifilm® assay. The sample is uniformly distributed by exerting light pressure at the center of the plastic diffuser. The inoculum is thus distributed over the entire growth zone before the gel forms.

TABLE 1

| | Dilution CFU/ml | | | | | | | |
|---|---|---|---|---|---|---|---|---|
| | $10^8$ | $10^7$ | $10^6$ | $10^5$ | $10^4$ | $10^3$ | $10^2$ | 10 |
| Colonies | ≥300 Not countable | ≥300 Not countable | ≥300 Not countable | ≥300 Not countable | ≥300 Not countable | ≥300 Not countable | 78 | 7 |

The results show that six dilutions are necessary in order to obtain isolated and usable colonies.

Example 2: Obtaining Isolated Colonies from a Heavily Contaminated Solution on a Rehydrated Medium According to the Present Invention Starting from the same solution calibrated at a theoretical bacterial load of $10^8$ CFU/ml used for inoculation of the Petrifilm®, mechanical inoculation by the "dial" method is carried out on the device according to the invention, allowing isolated colonies to be obtained on a limited area (25 cm$^2$) of the device.

Thus, the device according to the invention was seeded with 10 µl (contents of one loop) of a solution calibrated at a theoretical bacterial load of $10^8$ CFU/ml loaded with *Escherichia coli* and deposited on the 1st dial 21 of the isolation surface of the device whose useful isolation area is 25 cm$^2$. The second dial 22 is seeded with a new loop, drawing several streaks starting from dial 21. The third dial 23 is seeded like the second without changing the loop. The 4th dial 24 is seeded with streaks not drawn starting from dial 22.

The device is formed by an isolating layer with hydrophobic/hydrophilic units 28 on which isolation is performed. The hydrophobic/hydrophilic units make it possible to improve isolation, notably on a small area (25 cm$^2$) by spatially delimiting the growth of the microorganisms.

A layer containing the rehydrated culture medium 25. A bottom layer impermeable to water 26 and a translucent top layer sealing the device 27.

Figure 2A:
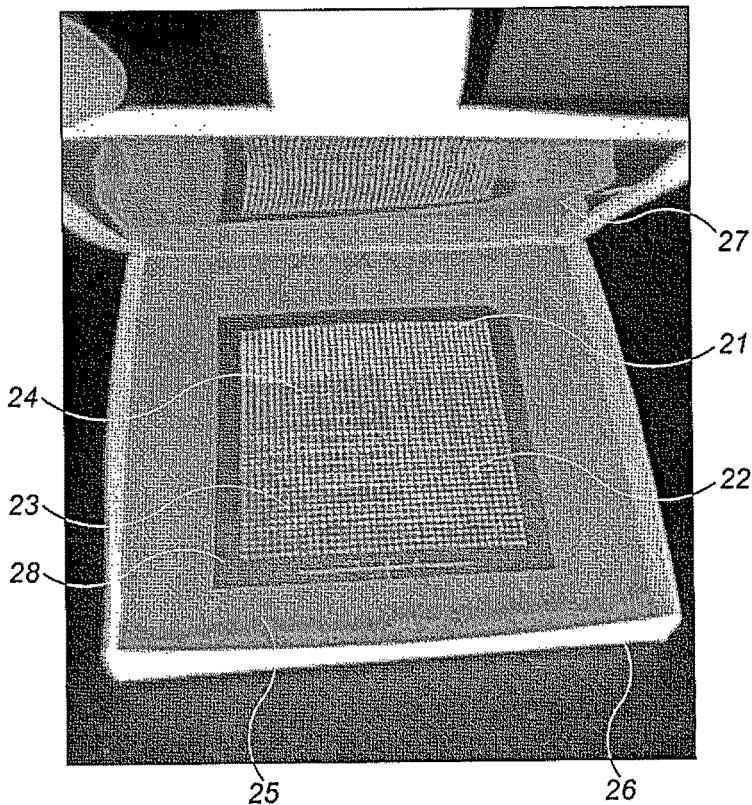
FIG. 2A is a photograph of the device according to the invention that has a useful isolation area of 25 $cm^2$.
Figure 2B:
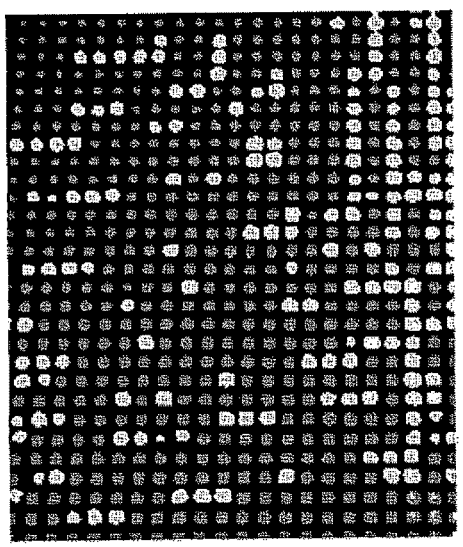
FIG. 2B shows an enlargement of the central portion of the device. The device was seeded with a sample of *Escherichia coli* at a concentration of $10^8$ CFU/ml.

FIGS. 2a and 2b show that the mechanical isolation on the device according to the invention allows formation of isolated colonies. Isolation is thus possible using a single device without prior dilution.

Example 3: Obtaining Isolated Colonies on an Isolating Layer of the Filtering Membrane Type, Arranged on a Nutrient Layer Consisting of a Nonwoven Support Impregnated with a Dehydrated Nutrient Medium The aim of this example is to compare the morphotypes and the growth time of colonies developing on a porous and/or filtering membrane (preferably filtering) positioned on an agar culture medium or on a nutrient layer impregnated with dehydrated culture medium.

The size and color of the colonies obtained from different bacterial species seeded on these porous and/or filtering membranes are evaluated by the operator.

3.1 Materials

The experiments described below notably relate to strains of *Escherichia coli*, *Clostridium freundii*, *Enterococcus faecalis*, *Klebsiella pneumoniae*, and *Enterobacter cloacae*.

The isolating layers tested for the present example comprise:

- a polyester filtering membrane (Macherey Nagel Polyester) comprising pores with a diameter of 0.2 µm, 0.4 µm, 1 µm and 5 µm (trade reference: PORAFIL® PE),
- a cellulose nitrate filtering membrane (Macherey Nagel Polyester) comprising pores with a diameter of 0.2 µm, 0.4 µm, 1 µm and 5 µm (trade reference: PORAFIL® NC),
- a cellulose acetate filtering membrane (Macherey Nagel Polyester) comprising pores with a diameter of 0.2 µm, 0.4 µm, 1 µm and 5 µm (trade reference: PORAFIL® CA),
- a filtering membrane of cellulose mixed esters (Macherey Nagel Polyester) comprising pores with a diameter of 0.2 µm, 0.4 µm, 1 µm and 5 µm (trade reference: PORAFIL® CM),
- a cellulose nitrate filtering membrane (Sartorius stedim Biotech) comprising pores with a diameter of 0.45 µm.

For the purposes of the present experiments, the following nonwoven supports are used:

Glatfelter, Airlaid 100 g/m$^2$,
Glatfelter, Airlaid concert 150 g/m$^2$,
PDI supports 60 g/m$^2$.

The culture media used for impregnating the nonwoven support in the present experiments are: a Trypcase soybean broth (TSB-D), a culture medium of the UriSelect® type 4 (trade reference: BioRad), or a culture medium of the Chrom ID CPS 3 type without agar.

The agar culture media used in the present experiments are as follows: UriSelect®4 (trade reference BioRad) and Chrom ID CPS 3.

3.2 Experimental Protocol

Firstly, the various filtering membranes are tested on an agar medium of the UriSelect® 4 type (cf. section 3.3.1 below).

Secondly, the UriSelect® 4 agar culture medium is replaced with the various nonwoven supports impregnated with a culture medium mentioned above (cf. section 3.3.2 below).

The nonwoven supports, impregnated with the culture medium, are rehydrated using a predetermined volume of sterile water and a bacterial inoculum at the moment of performing the analysis. The volume/amount of sterile water necessary for rehydration of the nonwoven support, impregnated with the culture medium, varies as a function of the nature of the nonwoven support and the size of the latter. This information can easily be determined by a person skilled in the art based on his general knowledge, and routine tests if necessary.

The assembly of filtering membrane and impregnated nonwoven support or filtering membrane and agar medium is incubated at a temperature of 37° C. Visual reading of the results for determining the morphotype of the colonies and quality of isolation on the surface of the porous and/or filtering membrane is carried out firstly after an incubation time of 24 h and then secondly after a total incubation time of 48 h.

3.3 Results 3.3.1 Isolation of Various Microorganisms on Different Types of Filtering Membranes, in the Presence of an Agar Culture Medium FIGS. 3, 4, 5 and 6 show isolation of a strain of *Klebsiella pneumoniae* in the presence of a UriSelect™ 4 agar culture medium, after an incubation time of 24 h.

Figure 3:
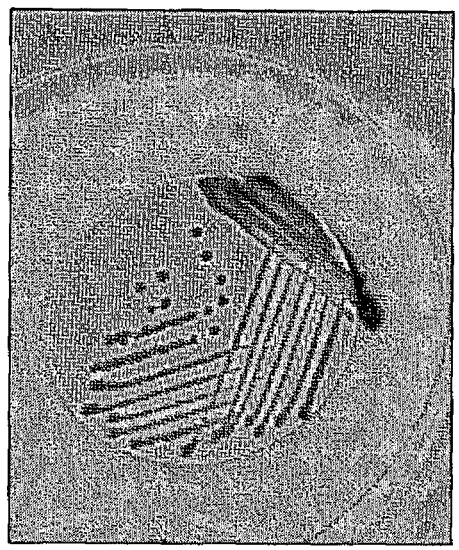
FIG. 3 shows the contents of a Petri dish seeded with a strain of *Klebsiella pneumoniae* in the presence of a UriSelect™ 4 culture medium with an isolating layer consisting of a Macherey Nagel cellulose nitrate filtering membrane, as an example.

More precisely, the filtering membrane in FIG. 3 is of cellulose nitrate (Macherey Nagel).

Figure 4:
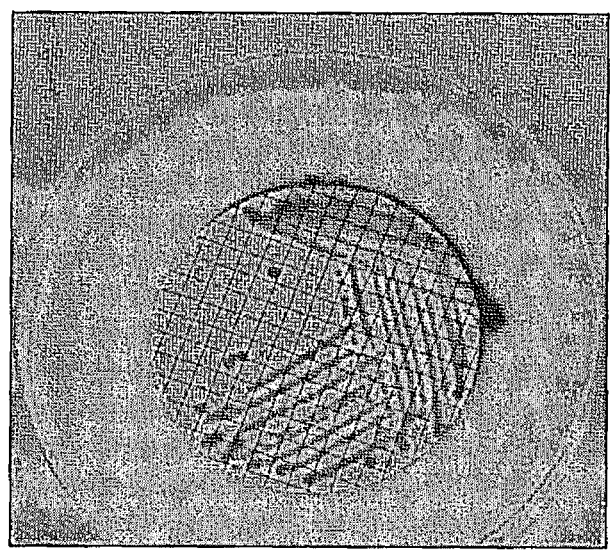
FIG. 4 shows the contents of a Petri dish seeded with a strain of *Klebsiella pneumoniae* in the presence of a UriSelect™ 4 culture medium with an isolating layer consisting of a Sartorius nitrate filtering membrane, as an example.

The filtering membrane in FIG. 4 is of Sartorius cellulose nitrate (Sartorius).

Figure 5:
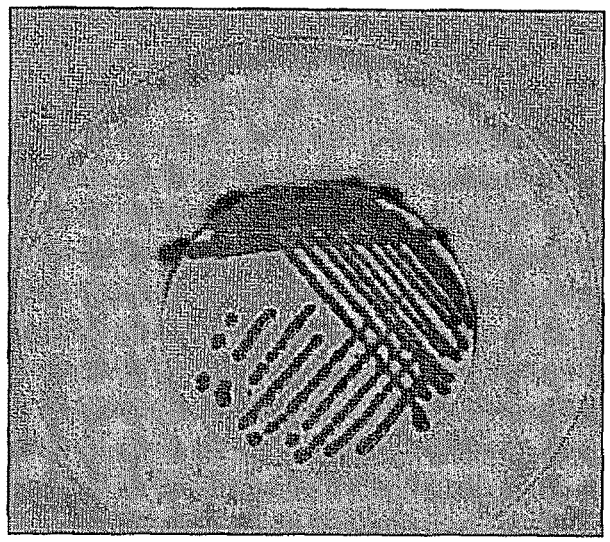
FIG. 5 shows the contents of a Petri dish seeded with a strain of *Klebsiella pneumoniae* in the presence of a UriSelect™ 4 culture medium with an isolating layer consisting of a cellulose acetate filtering membrane, as an example.
Figure 6:
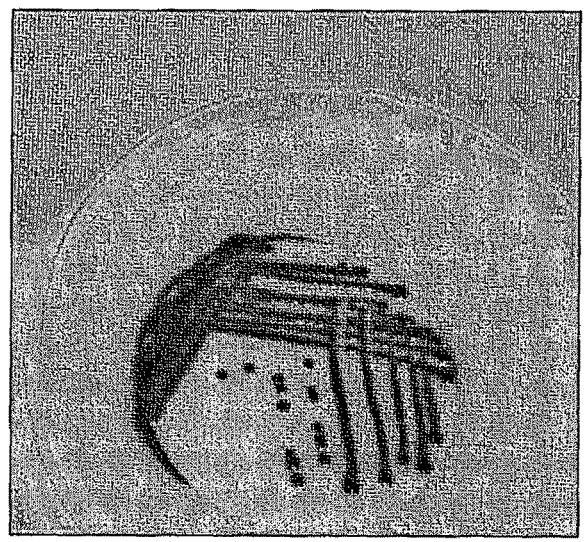
FIG. 6 shows the contents of a Petri dish seeded with a strain of *Klebsiella pneumoniae* in the presence of a UriSelect™ 4 culture medium with an isolating layer consisting of a polyester filtering membrane.

The filtering membrane in FIG. 5 is of cellulose acetate.
The filtering membrane in FIG. 6 is of polyester.

In these FIGS. 3, 4, 5 and 6, the presence of well individualized colonies that are directly usable (CDU) is noted.

FIGS. 7, 8, 9 and 10 show the presence of *Escherichia coli* in the presence of a UriSelect™ 4 agar culture medium, after an incubation time of 24 h.

Figure 7:
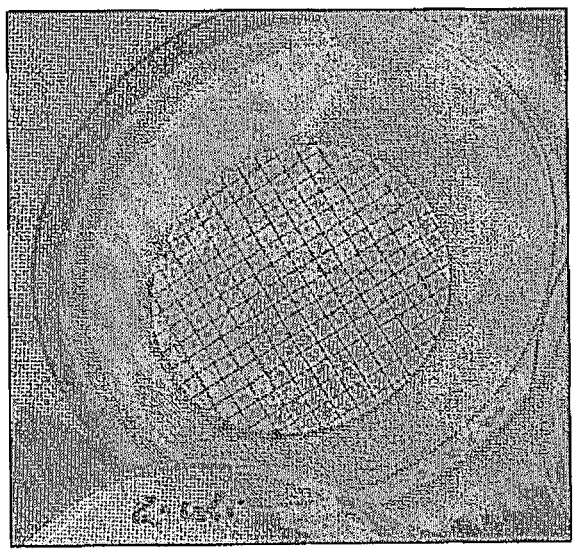
FIG. 7 shows the contents of a Petri dish seeded with a strain of *Escherichia coli* in the presence of a UriSelect™ 4 culture medium with an isolating layer consisting of a Macherey Nagel cellulose nitrate filtering membrane, as an example.

More precisely, the filtering membrane in FIG. 7 is of Macherey Nagel cellulose nitrate.

Figure 8:
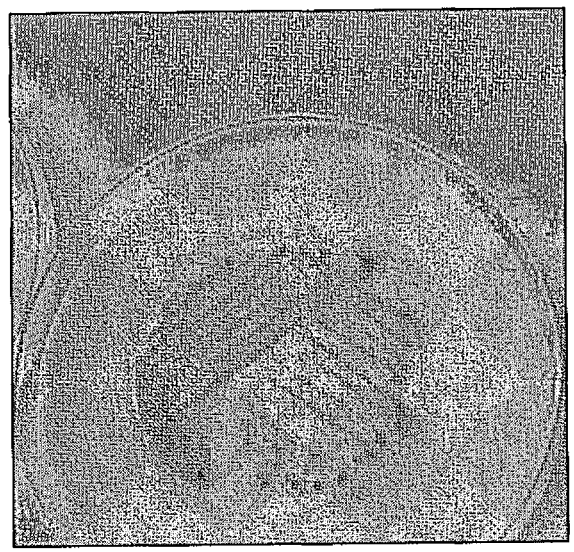
FIG. 8 shows the contents of a Petri dish seeded with a strain of *Escherichia coli* in the presence of a UriSelect™ 4 culture medium with an isolating layer consisting of a polyester filtering membrane, as an example.
Figure 9:
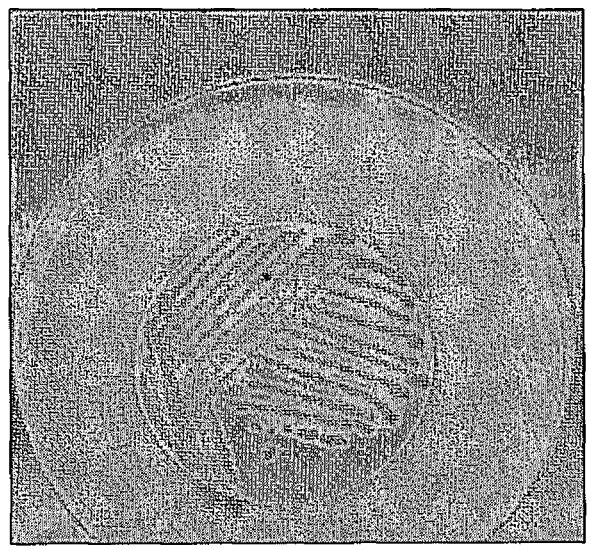
FIG. 9 shows the contents of a Petri dish seeded with a strain of *Escherichia coli* in the presence of a UriSelect™ 4 culture medium with an isolating layer consisting of a cellulose acetate filtering membrane, as an example.
Figure 10:
FIG. 10 shows the contents of a Petri dish seeded with a strain of *Escherichia coli* in the presence of a UriSelect™ 4 culture medium with an isolating layer consisting of a polyester filtering membrane, as an example.

The filtering membrane in FIG. 8 is of polyester.
The filtering membrane in FIG. 9 is of cellulose acetate.
The filtering membrane in FIG. 10 is of polyester.

In these FIGS. 7, 8, 9 and 10, the presence of well individualized colonies that are directly usable (CDU) is noted. The bacterial growth is optimal, the morphotypes and growth of the colonies obtained comply with what is expected of microbial growth directly on agar medium. Isolation performed on a porous and/or filtering membrane leads to morphotypes of colonies and a quality of isolation that are obtained conventionally with isolation carried out directly on agar medium.

3.3.2 Isolation and Count/Counting of Microorganisms on Filtering Membranes Deposited on Nonwoven Supports Impregnated with a Dehydrated Culture Medium The present experiments bring an impregnated nonwoven support into contact with a dehydrated culture medium. While the analysis is carried out, the nonwoven support is impregnated with water in order to rehydrate the culture medium.

Figure 11:
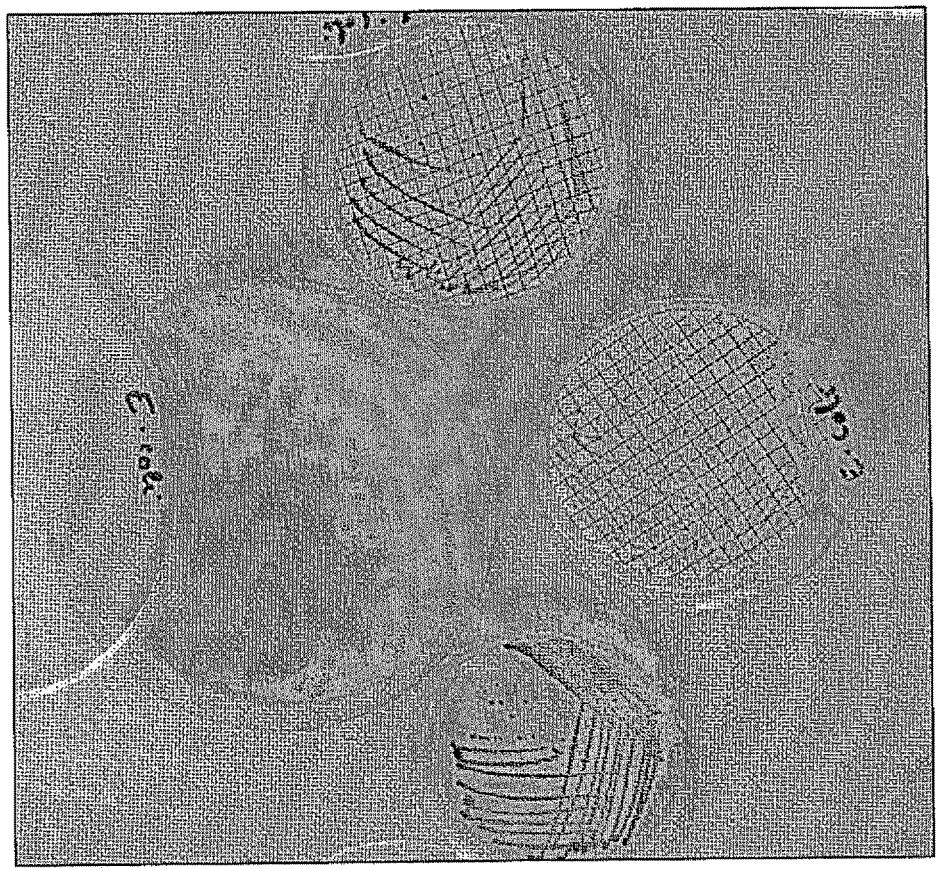
FIG. 11 shows the contents of four Petri dishes in the presence of a UriSelect™ 4 agar culture medium and of a dehydrated UriSelect™ 4 culture medium impregnated on a nutrient layer comprising a nonwoven support of the Glatfelter type, Airlaid 150 $g/m^2$ in the presence of a sample of a strain of *Escherichia coli*, as an example.

As shown in FIG. 11, the impregnation support used is of the Glatfelter type, Airlaid 150 g/m$^2$. The latter is impregnated with UriSelect™ 4 dehydrated culture medium.

The contents of the Petri dishes shown in FIG. 11 provide evidence of growth of the *Escherichia coli* bacteria and the presence of well individualized colonies that are directly usable (CDU).

Figure 12:
FIG. 12 shows the contents of four Petri dishes in the presence of a UriSelect™ 4 agar culture medium, of a dehydrated UriSelect™ 4 culture medium impregnated in a nutrient layer comprising a nonwoven support of the Glatfelter type, Airlaid 150 $g/m^2$ in the presence of a sample of a strain of *Enterobacter cloacae*, as an example.

FIG. 12 shows similar results in the presence of *Enterobacter cloacae* bacteria.

Figure 13:
FIG. 13 shows details of FIG. 16, showing the contents of two Petri dishes, as an example.

FIG. 13 shows results similar to those in FIGS. 11 and 12, in the presence of an agar medium of the UriSelect™ 4 type.

Figure 14:
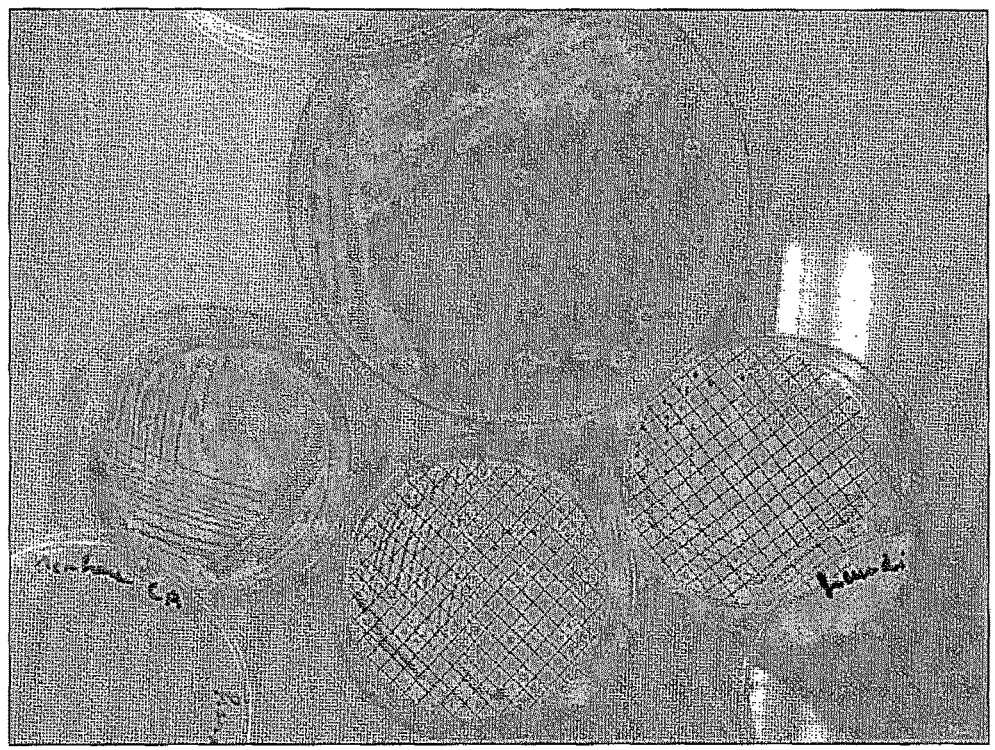
FIG. 14 shows the contents of four Petri dishes in the presence of an impregnated UriSelect™ 4 culture medium in a nutrient layer comprising a nonwoven support of the Glatfelter type, Airlaid 150 $g/m^2$ in the presence of an isolating layer such as a cellulose acetate filtering membrane and in the presence of a sample of a strain of *Clostridium freundii*, as an example.

Similar results can also be seen for the contents of the Petri dishes shown in FIG. 14 in the presence of a UriSelect™ 4 culture medium impregnated dry in a nonwoven support of the Glatfelter type, Airlaid 150 g/m$^2$ in the presence of a cellulose acetate filtering membrane.

Figure 15:
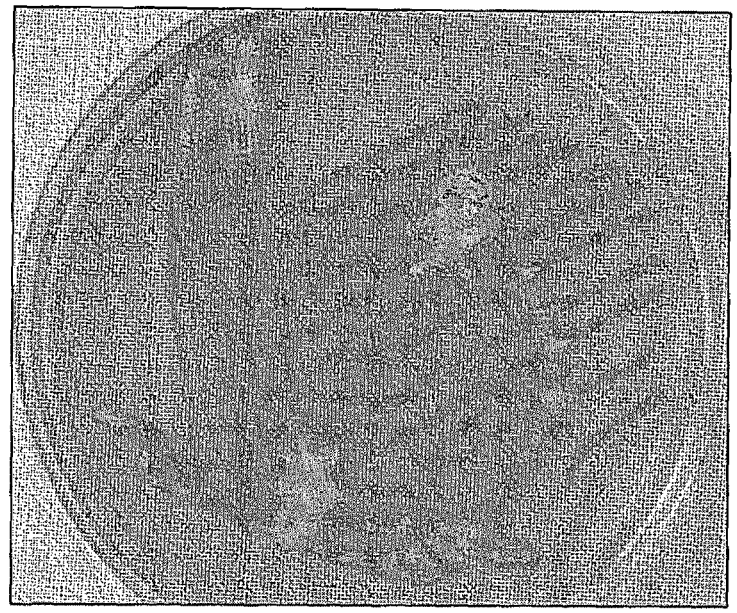
FIG. 15 shows the contents of a Petri dish comprising a nutrient layer containing a nonwoven support impregnated with an agar culture medium of the Chrom ID CPS ID3 type in the presence of a sample of *Enterococcus faecalis*, as an example.
Figure 16:
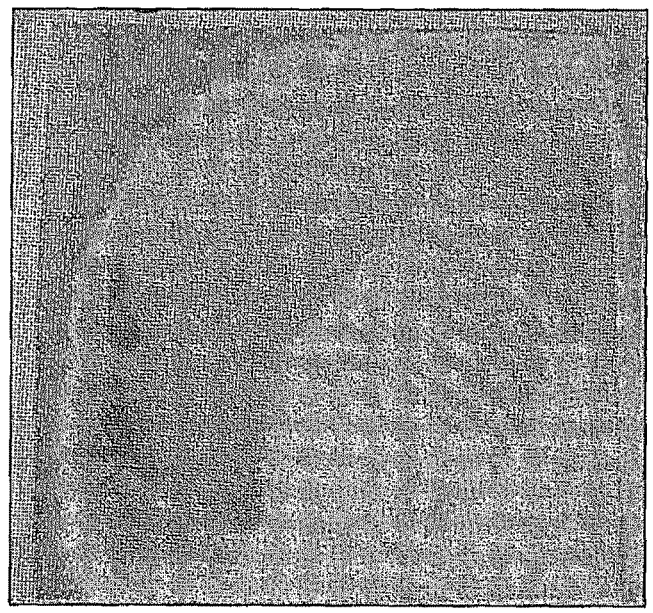
FIG. 16 shows the contents of a Petri dish comprising a nutrient layer containing a nonwoven support of the type Airlaid MH 100 137 impregnated with a culture medium of the Chrom ID CPS3 type, dehydrated and without agar.

3.3.3 Impregnation with a Culture Medium of the Chrom ID CPS ID3 Dehydrated Type The present experiments relate to a sample of *Enterococcus faecalis* in the presence of a Chrom ID CPS ID3 agar culture medium (cf. FIG. 15) and a dehydrated Chrom ID CPS3 medium without agar impregnated in the nonwoven support in the presence of a polyester filtering membrane (cf. FIG. 16).

Figure 17:
FIG. 17 shows the contents of a Petri dish in the presence of a culture medium of the Chrom ID CPS ID3 agar medium type and of a nutrient layer comprising a nonwoven support impregnated with a medium of the ChromID CPS3 type, dehydrated and without agar, in the presence of an isolating layer such as a polyester filtering membrane and a sample of a strain of *Enterobacter cloacae*, as an example.

Another experiment relates to a sample of *Enterobacter cloacae* in the presence of an agar culture medium of the Chrom ID CPS ID3 type and a culture medium impregnated with the Chrom ID CPS3 dehydrated type without agar in the presence of a polyester filtering membrane (cf. FIG. 17). In FIG. 17, the presence of well individualized colonies that are directly usable (CDU) is noted.

Figure 18:
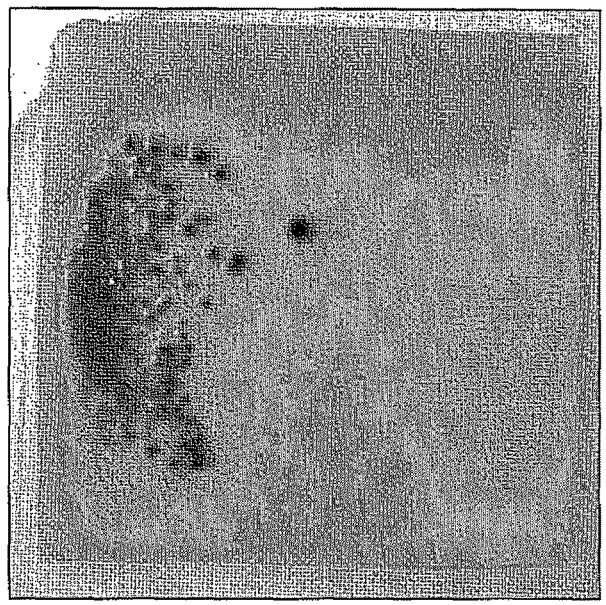
FIG. 18 shows details of a nutrient layer comprising a nonwoven support of the Airlaid MH 100 137 type impregnated with a culture medium of the Chrom ID CPS ID3 type without agar and in the presence of an isolating layer such as a polyester membrane.
Figure 19:
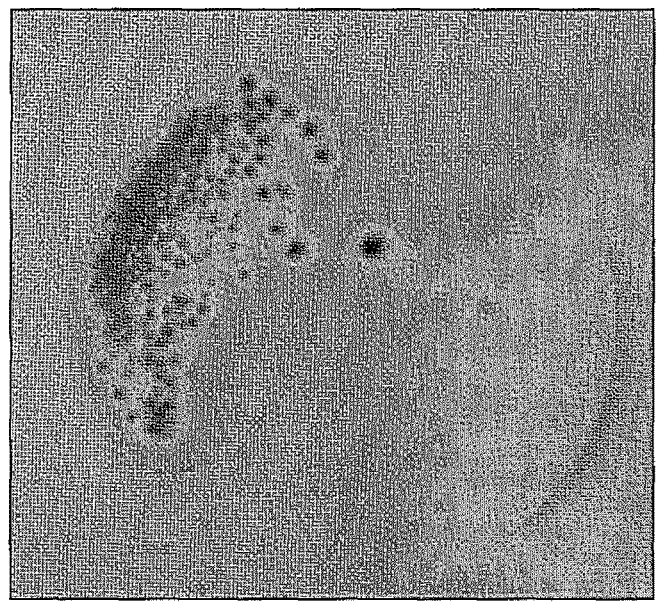
FIG. 19 shows another example of support according to FIG. 18.

FIGS. 18 and 19 show the results of an experiment bringing a Chrom ID CPS ID3 culture medium without agar impregnated on an Airlaid MH 100 137 nonwoven support in the presence of a polyester filtering membrane.

As shown in FIGS. 18 and 19, the presence of well individualized colonies that are directly usable (CDU) is noted. Although isolation was carried out on filtering membranes positioned on dehydrated culture media—and not on agar media—this did not affect bacterial growth, which proved to be optimal. Moreover, the morphotypes of the colonies obtained are similar to those obtained with isolation on porous and/or filtering membranes positioned on agar medium.

3.4 Conclusions

The results of the experiments relating to example 3 indicate that it is possible to perform isolations of microorganisms on an isolating layer of the filtering membrane type. It should be noted that these filtering membranes are not used for the action of filtration of liquid, which is their primary use, but for carrying out isolation of a sample that may be heavily laden with microorganisms, which requires them to have the same surface qualities as those that are obtained on agar media. Moreover, isolation did not generate deformations of the filtering membrane, the latter remaining as if glued to the underlying nutrient layer (nutrient support)

without requiring any physical or chemical bond between the filtering membrane and the nutrient layer. This intimate proximity of the filtering membrane with the nutrient layer after isolation is verified when we examine the integrity and continuity of the isolation path through the arrangement of the bacterial colonies.

Besides compatibility of the porous and/or filtering membranes with the operation of microbial isolation, the applicant has demonstrated that the superposition of the isolating layer of the filtering membrane type and the nutrient layer of the nonwoven support type impregnated with dehydrated culture medium allows optimal growth of the microorganisms on the isolating layer, as evidenced by the morphotypes of the bacterial colonies obtained.

It also appears that the nonwoven support impregnated with a dehydrated culture medium represents a valid alternative to culturing microorganisms in the presence of a gelose culture medium containing agar. In fact, the nutrient layer allows exchanges of nutrients with the microorganisms located on the isolating layer in order to allow quality microbial growth. Thus, the presence of an isolating layer arranged above a nutrient layer impregnated with a dehydrated culture medium makes it possible to obtain isolated colonies of microorganisms on the surface of the isolating layer. The porosity of the filtration membrane allows retention of the microorganisms on its surface and the transfer of the dissolved nutrients present in the nutrient support to the surface of the filtration membrane. Example 3 clearly demonstrates that such transfers are optimal as no delay of growth suggested notably by a reduced size of the colonies was observed. Note once again that this transfer is optimal in the absence of bonding means or binder between filtration membrane and nutrient layer.

In general, the exchanges of nutrients and of water between the nutrient layer and the filtering membrane allow optimal microbial growth. The impregnated culture medium is rehydratable or may be rehydrated a short time before or simultaneously with microbial isolation.

Example 3 notably demonstrates that the device according to the invention is compatible with isolation and microbial growth.

The invention claimed is:

1. A method for isolating at least one microorganism from a sample, comprising:
   (a) supplying a device for isolation of at least one microorganism, the device comprising
      a bottom layer impermeable to water;
      a nutrient layer, arranged on the bottom layer, comprising a support impregnated with a calendered, dehydrated culture medium;
      an isolating layer permeable to the elements comprised in the nutrient layer, able to retain the at least one microorganism on its surface and covering the whole or a portion of the nutrient layer; and
      a protective top layer;
   (b) depositing a defined volume of the sample on the isolating layer;
   (c) isolating the at least one microorganism by exhaustion or by coating the sample using isolating means;
   (d) incubating the device for a predetermined time and at a predetermined temperature allowing growth of the at least one microorganism; and
   (e) rehydrating the culture medium with a predetermined volume of liquid before or simultaneously with one or more of step (b), step (c), and step (d).

2. The method as claimed in claim 1, wherein the isolating layer has hydrophilic and/or hydrophobic units.

3. The method as claimed in claim 1, wherein the device also comprises an identification code.

4. The method as claimed in claim 3, wherein the identification code is a barcode or a radio-frequency identification (RFID) tag.

5. The method as claimed in claim 1, wherein the liquid used for rehydrating the culture medium is an aqueous solution and/or a liquid containing microparticles with lipid envelopes.

6. The method as claimed in claim 1, wherein at least the nutrient layer and the isolating layer are mechanically independent of one another within said device.

* * * * *